United States Patent [19]

Haag et al.

[11] Patent Number: 5,243,090
[45] Date of Patent: * Sep. 7, 1993

[54] CONVERSION OF NORMAL ALKENES TO TERTIARY ALKYL ETHERS

[75] Inventors: Werner O. Haag, Lawrenceville, N.J.; Mohsen N. Harandi, Langhorne, Pa.; Hartley Owen, Belle Mead, N.J.

[73] Assignee: Mobil Oil Corporation, Fairfax, Va.

[*] Notice: The portion of the term of this patent subsequent to Jul. 21, 2009 has been disclaimed.

[21] Appl. No.: 914,973

[22] Filed: Jul. 16, 1992

Related U.S. Application Data

[63] Continuation-in-part of Ser. No. 665,052, Mar. 6, 1991, Pat. No. 5,123,467.

[51] Int. Cl.$^5$ ............................................. C07C 41/05
[52] U.S. Cl. ..................................................... 568/697
[58] Field of Search ........................................ 568/697

[56] References Cited

U.S. PATENT DOCUMENTS

| | | | |
|---|---|---|---|
| 4,232,177 | 11/1980 | Smith | 585/324 |
| 4,504,687 | 3/1985 | Jones | 568/697 |
| 4,544,776 | 10/1985 | Osterburg et al. | 568/697 |
| 4,554,386 | 11/1985 | Groeneveld et al. | 568/697 |
| 4,665,237 | 5/1987 | Arakawa et al. | 568/697 |
| 4,684,757 | 8/1987 | Avidan | 585/331 |
| 4,816,607 | 3/1989 | Vora et al. | 568/697 |
| 4,925,455 | 5/1990 | Harandi | 44/77 |
| 4,975,097 | 12/1990 | Harandi et al. | 568/697 |
| 5,132,467 | 7/1992 | Haag et al. | 568/697 |

Primary Examiner—Howard T. Mars
Attorney, Agent, or Firm—Alexander J. McKillop; Dennis P. Santini; Laurence P. Hobbes

[57] ABSTRACT

A process is disclosed for the production of tertiary alkyl ethers wherein linear olefins, particularly n-butene, are isomerized in the vapor phase at high temperature in contact with shape selective metallosilicate catalyst to produce iso-olefin vapor, particularly isobutene. The vaporous iso-butene is then etherified with alkanol to provide alkyl tert-alkyl ether such as MTBE. Unreacted iso-olefin and/or linear olefin and product ether are separated by fractionation and unreacted olefin components recycled. Fractionation of the vapor phase etherification product is carried out by using the fresh liquid linear olefin feedstream as a reflux stream to the fractionator.

19 Claims, 1 Drawing Sheet

CONVERSION OF NORMAL ALKENES TO TERTIARY ALKYL ETHERS

REFERENCE TO COPENDING APPLICATION

This application is a continuation-in-part of copending U.S. patent application Ser. No. 07/665,052, filed Mar. 6, 1991, now U.S. Pat. No. 5,132,467, the entire contents of which are incorporated herein by reference.

FIELD OF THE INVENTION

This invention relates to an integrated process for the production of alkyl tertiary alkyl ethers. The invention particularly relates to an integrated process for converting a feedstock containing linear olefins and iso-olefins to high octane tertiary alkyl ethers. More particularly, the invention relates to the conversion of linear and branched alkenes in $C_4$, $C_5$, $C_4+$ or $C_5+$ feedstock to $C_5+$ gasoline components containing methyl tertiary butyl ether (MTBE) and/or tertiary amyl methyl ether (TAME).

BACKGROUND OF THE INVENTION

It is known that isobutylene and other isoalkenes, or iso-olefins, produced by hydrocarbon cracking may be reacted with methanol and other $C_1$-$C_4$ lower aliphatic alcohols, or alkanol, over an acidic catalyst to provide methyl tertiary butyl ether (MTBE) or the like. Generally, it is known that asymmetrical ethers having the formula $(CH_3)_3C-O-R$, where R is a $C_1$-$C_4$ alkyl radical, are particularly useful as octane improvers for liquid fuels, especially gasoline.

MTBE, ethyl t-butyl ether (ETBE), tert-amyl methyl ether (TAME) and isopropyl t-butyl ether (IPTBE) are known to be high octane ethers. The article by J. D. Chase, et al., *Oil and Gas Journal*, Apr. 9, 1979, discusses the advantages one can achieve by using such materials to enhance gasoline octane. The octane blending number of MTBE when 10% is added to a base fuel $(R+O=91)$ is about 120. For a fuel with a low motor rating $(M+O=83)$ octane, the blending value of MTBE at the 10% level is about 103. On the other hand, for an $(R+O)$ of 95 octane fuel, the blending value of 10% MTBE is about 114.

The reaction of tertiary olefins with alkanol to produce alkyl tertiary alkyl ether is selective with respect to iso-olefins. Linear olefins are unreactive in the acid catalyzed reaction, even to the extent that it is known that the process can be utilized as a method to separate linear and iso-olefins. The typical feedstream of FCC $C_4$ or $C_4+$ crackate used to produce tertiary alkyl ethers in the prior art and containing normal butene and isobutene utilizes only the branched olefin in etherification. This situation presents an exigent challenge to workers in the field to discover a technically and economically practical means to utilize linear olefins, particularly normal butene, in the manufacture of tertiary alkyl ethers.

In recent years, a major development within the petroleum industry has been the discovery of the special catalytic capabilities of a family of zeolite catalyst based upon medium pore size shape selective metallosilicates. Discoveries have been made leading to a series of analogous processes drawn from the catalytic capability of zeolites. Depending upon various conditions of space velocity, temperature and pressure, lower oxygenates such as methanol can be converted in the presence of zeolite type catalyst to olefins which can oligomerize to provide gasoline or distillate or can be converted to produce aromatics or isomerization products. Recognizing the commonality of the feedstock and product between etherification reactions to produce high octane gasoline and zeolite catalyzed conversion reactions, interest has focused on the applicability of combined processes as an approach to advance the art in the production of high octane gasoline.

European Patent 0026041 to Garwood, incorporated herein by reference, discloses a process for the restructuring of olefins in contact with zeolite catalyst to produce iso-olefins, followed by the conversion of iso-olefins to MTBE and TAME. The restructuring conditions comprise temperature between 204° C. and 315° C. and pressure below $5.1 \times 10^4$ kPa. In European Patent 0247802 to Barri et al., it is taught that linear olefins can be restructured in contact with zeolite catalyst, including ZSM-23, to produce branched olefins. The restructuring conditions comprise temperature between 200°-550° C., pressure between 100 and 1000 kPa and WHSV between 1 and 100. It is taught that in the process 1-butene conversion exceeds 59 mole % with a selectivity to isobutene greater than 52 mole %.

It has been discovered that under certain conditions substantial improvements in the art of alkyl tert-alkyl ether production can be realized in a combination or integration of etherification and hydrocarbon conversion processes based upon zeolite type catalysis. In U.S. Pat. Nos. 4,788,365, 4,826,507 and 4,854,939 to M. N. Harandi and H. Owen novel processes are described for carrying out the production of MTBE and TAME wherein unreacted alcohol and light olefin components from the etherification reaction are converted to higher hydrocarbons in contact with zeolite catalyst. These patents are incorporated herein by reference. In these processes the etherification reaction is carried out using $C_4+$ hydrocarbon feedstream rich in iso-olefins with the subsequent oligomerization of unreacted light olefins.

U.S. Pat. No. 4,605,787 to Chu et al., incorporated herein by reference, describes a process for the preparation of methyl tertiary butyl ether which comprises reacting isobutylene and methanol in the vapor phase in the presence of zeolite catalyst. Under the conditions described for the vapor phase etherification, side reactions, particularly the dimerization of isobutylene, are virtually eliminated. The reaction products are essentially MTBE and unreacted methanol and/or isobutylene.

It is an object of the present invention to provide a process for the etherification of linear olefins, particularly n-butene, to alkyl tertiary alkyl ether, particularly MTBE.

It is another object of the invention to provide a process for the isomerization of linear olefins to iso-olefins followed by the etherification of the iso-olefins so formed to provide alkyl tert-alkyl ethers.

Yet another object of the instant invention is to provide an integrated process for the etherification of linear and branched olefin components of a hydrocarbon feedstream by combining sequential etherification reactions with linear olefin isomerization to produce alkyl tert-alkyl ether, particularly MTBE.

A further object of the present invention is to carry out the foregoing objectives in a technologically practical and economically advantageous process configuration.

SUMMARY OF THE INVENTION

It has been discovered that the foregoing objectives can be accomplished in a process wherein linear olefins, particularly n-butene, are isomerized in the vapor phase at high temperature in contact with shape selective metallosilicate catalyst to produce iso-olefin, particularly vapor containing isobutene. The vaporous isobutene is then etherified with alkanol to provide alkyl tert-alkyl ether such as MTBE. The etherification of iso-olefin is preferably carried out in vapor phase or mixed liquid-vapor phase. The unreacted iso-olefin and/or linear olefin and product ether are separated by fractionation and unreacted olefin components recycled. It has been found particularly advantageous to facilitate the fractionation of the vapor phase etherification product by using the fresh liquid linear olefin feedstream as a reflux stream to the fractionator.

The foregoing combination of vapor phase conversion steps, i.e., isomerization and etherification, with a unique fractionation step surprisingly produces an overall process wherein pressure drop and heat input to the system are minimized as are the number and complexity of process equipment, while the overall process conversion and ether selectivity are very high.

In one embodiment of the invention a portion of the reflux in the fractionator comprises the reactor effluent from a liquid phase iso-olefin etherification zone containing alkyl tert-alkyl ether and unreacted linear olefin such as n-butene. As a result, the single fractionator is used to separate product from both vapor phase and liquid phase etherification while providing, as an overhead stream, the feedstream to the isomerization zone containing zeolite catalyst at high temperature. A portion of the overhead stream which contains paraffins can be dehydrogenated and the olefins so formed recycled to the isomerization zone. This combination of process steps maximizes the utilization of linear and branched olefins and paraffins in the feedstream to produce alkyl tertiary alkyl ethers.

More particularly, a continuous integrated process is disclosed for producing alkyl tertiary alkyl ether from alkanol and hydrocarbon feedstock containing linear olefins and iso-olefins, such as FCC or other cracking process $C_4$–$C_5$ product streams, comprising the steps of: contacting alkanol and hydrocarbon feedstock rich in iso-olefin with acid etherification catalyst under liquid phase iso-olefin etherification conditions in an etherification reaction zone. The etherification reaction effluent is separated in combination with an etherification reaction effluent from a vapor or mixed phase iso-olefin etherification reaction zone. The etherification reaction effluents are preferably separated in a common or single fractionator. An overhead vapor stream is recovered comprising linear olefins plus a liquid product bottom stream comprising alkyl tertiary alkyl ether. The overhead stream is contacted with acidic, medium pore metallosilicate catalyst in an isomerization zone under linear olefins isomerization conditions sufficient to convert the linear olefins to iso-olefins. The isomerization conditions comprise a temperature of about 300° C. to 700° C. (preferably at least 350° C. or 400° C. to 600° C.), an olefin partial pressure between about 20 kPa and 1500 kPa and a weight hourly space velocity between 5 and 500, say, 20 and 500, (preferably about 100 to 200). The isomerization reaction effluent is etherified along with fresh alkanol feedstream in a vapor or mixed vapor/liquid phase iso-olefin etherification condition to provide an etherification reaction effluent fractionated as described above. Preferably, at least a portion of etherification occurs over a bed of acid catalyst disposed in the fractionator.

The foregoing process is carried out in a unique reactor system for the production of alkyl tertiary alkyl ethers from alkanol feedstock and a hydrocarbon feedstream containing $C_4+$ linear olefins, comprising in combination: a means for introducing a vapor feedstream comprising said linear olefins to an isomerization zone containing shape selective metallosilicate catalyst particles under conditions sufficient to convert said linear olefins to $C_4+$ iso-olefins; a means for passing the vaporous reaction effluent rich in iso-olefins from said isomerization zone and an alkanol feedstream to a vapor phase or mixed phase iso-olefin etherification zone in contact with acidic etherification catalyst under etherification conditions whereby said alkyl tertiary alkyl ether is produced; a means for separating said etherification zone reaction effluent in a fractionator which preferably contains a bed of acid etherification catalyst, and recovering a bottom stream comprising said tertiary alkyl ether; and a means for recycling a portion of said fractionator overhead stream containing $C_4$ linear olefins to said isomerization zone. The reactor system can also contain a means to purge a portion of the unconverted feed from the system.

DETAILED DESCRIPTION OF THE INVENTION

Figure 1:
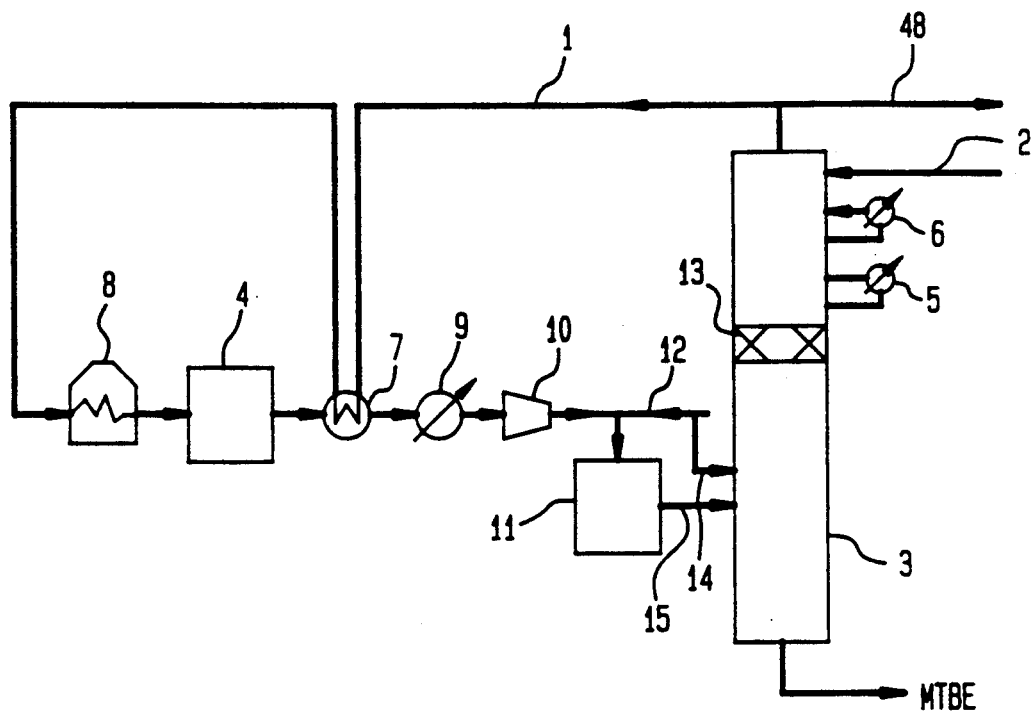
FIG. 1 is a schematic process flow diagram of the present invention illustrating the integration of vapor phase isomerization with vapor phase etherification and the unique fractionator system of the invention.

The present invention provides a process which utilizes both linear olefins and/or iso-olefins in a $C_4$, $C_5$, $C_4+$ or $C_5+$ hydrocarbon feedstream for the production of lower alkyl tert-butyl ether by alkanol etherification. Etherification of linear olefins is accomplished by isomerization using a unique zeolite catalyzed vapor phase isomerization process to produce iso-olefins which are then etherified in contact with zeolite catalyst in the vapor phase or mixed liquid-vapor phase to produce alkyl tert-butyl ethers. The mixed liquid-vapor phase etherification step is preferably carried out employing acid catalyst contained in an upper portion of a debutanizer used in the separation and recovery of the tertiary alkyl ether product. Vapor phase or mixed liquid-vapor phase containing at least 5 wt. % vapor etherification processes may be utilized singly or in combination in the process of the invention.

Linear olefins may be derived from a fresh feedstream, preferably comprising n-butene, or from the effluent of a liquid phase iso-olefin etherification reactor which employs alkanol and $C_4$, $C_5$, $C_4+$ or $C_5+$ hydrocarbon feedstock.

The feedstock to the etherification step of the present invention includes lower alkanol and $C_4+$ hydrocarbons rich in iso-olefins. Typical hydrocarbon feedstock materials for etherification reactions according to the present invention include olefinic streams, such as cracking process light gas containing butene isomers in mixture with substantial amounts of paraffins including n-butane and isobutane. The $C_4$ components usually contain a major amount of unsaturated compounds, such as 10–40% isobutylene, 20–55% linear butenes, and small amounts of butadiene. Also, $C_4+$ heavier olefinic hydrocarbon streams may be used, particularly mixtures of isobutylene and isoamylene. Suitable alkanols include lower aliphatic $C_1$–$C_4$ primary or secondary alcohols, but preferably methanol.

The liquid phase reaction of methanol with isobutylene and isoamylenes at moderate conditions with a resin catalyst is known technology, as provided by R. W. Reynolds, et al., *The Oil and Gas Journal*, Jun. 16, 1975, and S. Pecci and T. Floris, *Hydrocarbon Processing*, December 1977. An article entitled "MTBE and TAME—A Good Octane Boosting Combo," by J. D. Chase, et al., *The Oil and Gas Journal*, Apr. 9, 1979, pages 149–152, discusses the technology. Preferred catalysts are polymeric sulfonic acid exchange resin such as Amberlyst 15 and zeolites such as zeolite Beta and ZSM-5. The acid resin catalysts are effective catalysts at temperatures below 90° C. At higher temperatures the resin catalyst is unstable.

As disclosed in the previously cited U.S. Pat. No. 4,605,787 to Chu et al., etherification of isobutene with methanol can be carried out in the vapor phase at temperatures between 77° C. and 105° C. in contact with acidic ZSM-5 or ZSM-11 to produce MTBE in high conversion and selectivity. The process is distinguished by the fact that the formation of isobutylene dimer byproduct is virtually eliminated.

In the etherification process it is known that alkanol and iso-olefins may be reacted in equimolar quantities or either reactant may be in molar excess to influence the complete conversion of the other reactant. Because etherification is an incomplete reaction the etherification effluent comprises unreacted alkanol and unreacted hydrocarbons. On a stoichiometric equivalency basis, equimolar quantities of methanol and iso-olefins are advantageous but an excess between 2 and 200% of either component can be passed to the etherification reaction unit. In the present invention, the molar ratio of alkanol to iso-olefin, such as methanol to iso-butylene, can be between 0.7 and 2, but preferably the molar ratio is 1 for methanol to isobutylene in liquid phase etherification. Advantageously, the excess methanol may be about 40% or more when the hydrocarbon feedstream comprises significant quantity of isoamylenes, but equimolar quantities are preferred when the hydrocarbon feedstream iso-olefin component consists essentially of $C_4$ hydrocarbons. In the instant invention, since a high recycle ratio is used and the feed is used as reflux to the fractionator, relatively high excess methanol can be used since the diluents present allow more methanol in the azeotropic mixture that can be formed in the tower.

Iso-olefins or isoalkenes in this invention are those having the formula $R_2C=CH_2$ or $R_2C=CHR$, particularly $C_4$–$C_7$ iso-olefins. Alkanols which may be used in the present invention include methanol, ethanol, 1-propanol, isopropanol, 1-butanol and 2-butanol. The term lower alkyl refers to $C_1$–$C_4$ alkyl including methyl, ethyl, n-propyl, isopropyl, n-butyl, sec-butyl, isobutyl and tert-butyl.

A distinguishing feature of the present invention is the utilization of an n-butene isomerization reaction step that evinces a surprisingly high selective conversion of n-butene to isobutene. It has been discovered that n-butene can be isomerized to iso-butene over a fixed bed of shape selective zeolite catalyst, particularly HZSM-23 shape selective metallosilicate catalyst, without significant oligomerization to heavier molecules. This phenomenon, it is believed, is a consequence of the pore structure of ZSM-23 which promotes isomerization at a much faster rate than the oligomerization of n-butene. Other acidic shape selective zeolites of similar pore structure are also useful in the isomerization of n-butene to isobutene according to this process, including ZSM-22, ZSM-35 (synthetic ferrierite), ZSM-48 and ZSM-34. However, HZSM-23 with an alpha value of about 1–20 is the preferred isomerization catalyst.

The isomerization reaction is preferably carried out at high temperature (at least 300° C., preferably 400° C. to 600° C.); high weight hourly space velocity based on olefin in the feed between 100 and 200/hr (WHSV); and relatively low olefin partial pressure (about 20 kPa to 500 kPa). The most preferred conditions are temperature of about 550° C., an olefin partial pressure of about 120 kPa and a WHSV of about 160. Under these optimized conditions the conversion of n-butene is greater than 29% and the selectivity to isobutene is about 90%.

The regeneration of spent zeolite catalyst used in the isomerization reaction is carried out oxidatively or hydrogenatively employing procedures known in the art.

Alpha value, or alpha number, of a zeolite is a measure of zeolite acidic functionality and is more fully described together with details of its measurement in U.S. Pat. No. 4,016,218, *J. Catalysis*, 6, pp. 278–287 (1966) and *J. Catalysis*, 61, pp. 390–396 (1980).

ZSM-5 is more particularly described in U.S. Reissue Pat. No. 28,341 (of original U.S. Pat. No. 3,702,886), the entire contents of which are incorporated herein by reference.

ZSM-11 is more particularly described in U.S. Pat. No. 3,709,979, the entire contents of which are incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

MCM-22 is described in U.S. Pat. No. 4,954,325 to M. K. Rubin and P. Chu, issued Sep. 4, 1990. It has a $SiO_2/Al_2O_3$ ratio of 10 to 150, usually 20 to 40, with a high Alpha value, usually above 150.

Using HZSM-23 catalyst having an alpha value of about 19, 1-butene was isomerized under the following set of conditions to provide the results tabulated in TABLE I.

TABLE I

| Conditions: | | | |
|---|---|---|---|
| Pressure (kPa gauge) | 21 | 35 | 56 |
| Temp (°C.) | 500 | 501 | 501 |
| Flow (cc/min) | 100 | 150 | 200 |
| Results: | | | |
| Conv. of n-$C_4=$, % | 38 | 33.5 | 30 |
| i-$C_4=$, % | 34.5 | 31.0 | 27.5 |
| Selectivity, i-$C_4=$, % | 90.6 | 92.3 | 93.0 |

Referring to FIG. 1, a simplified process flow diagram for a preferred embodiment of the invention is presented for the vapor phase isomerization of n-butene to isobutene and vapor phase followed by mixed phase etherification of isobutene with methanol to produce methyl tert-butyl ether. In Table II a material balance is presented for the process shown in FIG. 1. As noted herein before, it has been discovered that the combination of vapor phase processes provides a means to design a practical integrated process containing acceptable pressure drops and energy requirements. When further combined with the depicted novel debutanizer design and operation, the integrated process provides a highly advantageous route to the conversion of linear and branched $C_4$ hydrocarbons to lower alkyl tert-butyl ether.

In FIG. 1, fresh feed 2 containing n-butene enters the top of the n-butene/MTBE debutanizer 3 where it is vaporized and sent along with the process recycle stream from the debutanizer overhead 1, at a pressure of preferably about 630 kPa and 44° C., to the isomerization reactor 4 containing a fixed bed of HZSM-23 catalyst. The feed vaporizing acts as a partial condenser for the debutanizer and creates some reflux within the tower to aid the fractionation. However, in many instances, vaporizing the feed does not provide all the required tower reflux. Therefore, optional pumparounds, 5 and 6, are incorporated into the design. This unique configuration minimizes pressure drop and saves the costs associated with a tower overhead system, condensing the process reflux stream and vaporizing the HZSM-23 reactor combined feed. The debutanizer overhead may also be chilled by using a chilled or refrigerated stream 2 which will allow operating the entire system at a lower total pressure, a factor that enhances selectivity.

The debutanizer overhead 1 is preheated to about 538° C. in heat exchanger 7 employing the effluent from the isomerization reactor 4. It is then heated to about 551° C. in fired heater 8 and the vapor introduced into the HZSM-23 fixed bed reactor at a pressure of about 720 kPa. A conversion of n-butene of about 38% per pass is achieved in the isomerization zone with about 84% selectivity to isobutene. Outlet conditions for the ZSM-23 reactor are about 554° C. and 525 kPa. The effluent is cooled 9 to about 38° C. at 470 kPa, compressed to 721 kPa at about 56° C. and passed to an optional vapor phase etherification zone 11, preferably containing HZSM-5 or zeolite Beta catalyst, for conversion to MTBE in conjunction with a methanol feedstream 12. The MTBE reactor effluent 15 containing unconverted isobutene and methanol is cooled to about 51° C. at a pressure of 651 kPa and sent to the debutanizer 3 where MTBE is further produced over a bed of acidic etherification catalyst and removed from the bottom of the tower as a liquid product 20. The debutanizer top section has a packed bed of acidic catalyst 13 to insure overall 95% isobutene conversion to MTBE. With a recycle to fresh feed ratio of about 9:1 for a fresh feed containing about 50% olefinic $C_4$'s, about 77% of n-butene in the fresh feed is converted to MTBE. Preferably, at least 50% of isobutene conversion occurs in the debutanizer reactor tower. The debutanizer overhead 1 is recycled back to the HZSM-23 reactor after the paraffins are purged out 48. Optionally, the purged paraffins can be dehydrogenated by means known in the art and the $C_4$ dehydrogenated fraction recycled to the debutanizer as a feedstock for conversion of linear butenes and isobutenes to MTBE; or the olefins content of the purge gas may be fractionated out of the purge stream and recycled to the system. As appropriate, a portion of the methanol feed 12 can be sent directly to the debutanizer via 14 to promote formation of MTBE in contact with the acidic catalyst in the debutanizer.

Table II presents feedstream and product quantities for the process of the instant invention.

TABLE II

| | N-Butene Isomerization/MTBE Process Feed and Products Mass Basis, Lbs/hr: | | |
|---|---|---|---|
| Components | Fresh Feed | MeOH | debutanized MTBE Product |
| C2— | | | |
| C3's | 2394 | | |
| isobutane | 27551 | | 213 |
| n-butene | 39330 | | 88 |
| n-butane | 6233 | | 1263 |
| isobutene | 995 | | 2 |
| 1-pentene | | | 554 |
| isopentene | | | 321 |
| methanol | 678 | 16823 | |
| MTBE | | | 47046 |
| TAME | | | 1104 |
| C6+ | | | 409 |
| TOTAL | 77181 | 16823 | 51000 |

The foregoing process of the invention uniquely achieves a balance of conversion, selectivity and process economics by optimizing recycle ratio and operating pressure. This is specifically achieved by operating the debutanizer overhead at an economically realizable pressure at which the tower overhead stream is a saturated vapor at about 30°-50° C. This allows the creation of a reflux in the tower while essentially the entire system is operated under vapor phase, and mixed phase in the tower.

Figure 2:
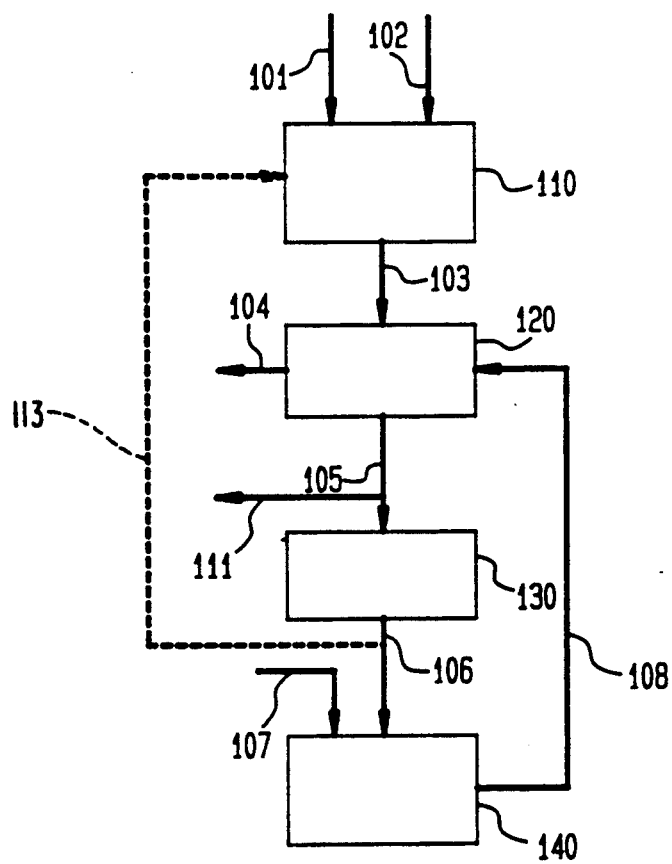
FIG. 2 is a block diagram depicting one embodiment of the present invention utilizing liquid phase and vapor or mixed phase etherification.

In another preferred embodiment of the invention the fresh feedstream to the debutanizer of the vapor phase isomerization and vapor phase etherification process comprises the effluent from a liquid phase MTBE reactor. The effluent is rich in n-butene which is converted to isobutene and etherified as described above. In this configuration a single, or common debutanizer, serves to separate the MTBE product from both the liquid phase and vapor phase etherification reactors. FIG. 2 illustrates the process.

Referring to FIG. 2, the major units of the process consist of a liquid phase MTBE reactor 110, a single debutanizer 120, placed upstream of an optional methanol recovery unit (not shown), a vapor phase n-butene isomerization zone 130 containing ZSM-23 catalyst, and a vapor phase MTBE reactor 140. Optionally, the process can contain a dehydrogenation reactor 150. A methanol feedstream 101 and a hydrocarbon feedstream 102 comprising $C_4$ or $C_4+$ linear olefins and iso-olefins is passed to the liquid phase etherification zone containing acidic catalyst for the production of MTBE under conditions known in the art. However, excess methanol (1-20%) is preferred in the liquid phase reactor of the design. The reactor effluent 103, which contains the MTBE and/or TAME product and unreacted linear olefins, particularly n-butene, is passed to the top section of debutanizer 120 in conjunction with the effluent from the optional vapor phase reactor 140 or the isomerization reactor effluent. In the common debutanizer MTBE and/or TAME are separated as products 104. The debutanizer overhead 105 is recycled to the isomerization zone 130 for conversion of n-butene to isobutene as previously described. The isomerization zone effluent 106 is passed to the MTBE vapor phase reactor in conjunction with methanol feedstream 107 for the conversion of isobutylene to MTBE and the isomerization zone effluent line may communicate with a purge line (not shown) for removal of unreacted components.

The effluent 108 from the vapor phase reactor 140 is passed to the debutanizer for separation of MTBE and recycle of unreacted n-butene. Optionally a portion of the debutanizer overhead is dehydrogenated in reactor 150 to provide C₄ linear and iso-olefins which are recycled to the liquid phase MTBE reactor. Unreacted components are removed by purge line 111. Optionally, as shown by the dashed line 113 in FIG. 2, all or a portion of the effluent from the isomerization zone 130 is passed directly to a liquid phase etherification zone 110 for conversion to MTBE. In this optional embodiment, conversion in the vapor phase etherification zone 140 is reduced or eliminated.

In those cases of the subject invention comprising MTBE and TAME production from C₄ and C₅ feedstreams, the feed can be fractionated to a C₄ rich stream and C₅ rich stream and two separate units employed to upgrade these streams. The C₅ unit uses a depentanizer to purify the TAME product and to recycle unconverted C₅ hydrocarbons.

While the instant invention has been described by specific examples and embodiments, there is no intent to limit the inventive concept except as set forth in the following claims.

We claim:

1. A continuous integrated process for producing alkyl tertiary alkyl ether from alkanol and hydrocarbon feedstock containing linear olefins and iso-olefins, comprising:
   (a) contacting said alkanol and said hydrocarbon feedstock with acid etherification catalyst under liquid phase iso-olefin etherification conditions in an etherification reaction zone, whereby a reaction effluent is produced comprising linear olefins, unconverted iso-olefins, alkanol and alkyl tertiary alkyl ether;
   (b) separating etherification reaction effluent from step (a) in combination with the etherification reaction effluent from step (d) iso-olefin etherification reaction zone in a common distillation fractionator and recovering an overhead vapor stream comprising linear olefins and a liquid product bottom stream comprising alkyl tertiary alkyl ether;
   (c) contacting said overhead stream with acidic, medium pore metallosilicate catalyst in an isomerization zone under linear olefins isomerization conditions sufficient to convert said linear olefins to iso-olefins, said conditions comprising a temperature of about 300° C. to 700° C., an olefin partial pressure between about 20 kPa and 500 kPa and WHSV between about 5 and 500; and
   (d) etherifying step (c) reaction effluent and fresh alkanol feedstream under vapor phase iso-olefin etherification conditions sufficient to provide an etherification reaction effluent comprising alkyl tertiary alkyl ether; and
   (e) separating step (d) reaction effluent in step (b) fractionator.

2. The process of claim 1 wherein said alkanol feedstock consists essentially of C₁–C₄ alkanol.

3. The process of claim 1 wherein step (c) conditions comprise a temperature of about 350° to 550° C., an olefin partial pressure of about 20 to 120 kPa and WHSV of about 100 to 160.

4. The process of claim 1 wherein step (c) catalyst has the structure of ZSM-35.

5. The process of claim 1 wherein the alkanol feedstock comprises methanol.

6. The process of claim 1 wherein step (b) alkyl tertiary-alkyl ether comprises methyl tertiary butyl ether.

7. A continuous process for the production of alkyl tertiary alkyl ethers from alkanol feedstock and a hydrocarbon feedstream containing C₄+ linear olefins, comprising the steps of:
   (a) introducing a vapor feedstream comprising said linear olefins to an isomerization zone containing shape selective metallosilicate catalyst having the structure of ZSM-35 under conditions sufficient to convert said linear olefins to C₄+ iso-olefins;
   (b) passing the step (a) reaction effluent rich in iso-olefins and an alkanol feedstream to a vapor phase iso-olefin etherification zone in contact with acidic etherification catalyst under etherification conditions whereby said alkyl tertiary alkyl ether is produced;
   (c) separating step (b) reaction effluent in a distillation fractionator and recovering a bottom stream comprising said tertiary alkyl ether and an overhead vapor stream.

8. The process of claim 7 including the further step of recycling a portion of said fractionator overhead stream containing C₄ linear olefins to step (a) isomerization zone.

9. The process of claim 7 wherein a top portion of said fractionator contains acidic etherification catalyst under etherification condition and step (b) reaction effluent is introduced into said fractionator below said catalyst, whereby unreacted alkanol and iso-olefins in step (b) effluent are converted to alkyl tertiary alkyl ether.

10. The process of claim 7 wherein step (c) fractionation is carried out in contact with a reflux stream comprising fresh C₄+ liquid linear olefins introduced into a top portion of said fractionator, whereby said fresh liquid olefins are vaporized and a portion of step (b) reaction effluent condensed.

11. The process of claim 10 wherein said fresh linear olefins comprise at least a portion of the reaction effluent from a process comprising: contacting alkanol and C₄+ hydrocarbon feedstock rich in iso-olefins with acid etherification catalyst under liquid phase iso-olefin etherification conditions in an etherification reaction zone.

12. The process of claim 11 including the further step of passing a portion of said fractionator overhead stream containing isobutane to a dehydrogenation zone containing dehydrogenation catalyst under dehydrogenation conditions whereby isobutane is converted to isobutene; and passing said isobutene to said liquid phase of mixed liquid-vapor phase iso-olefin etherification zone.

13. The process of claim 7 wherein said isomerization zone comprises a fixed catalyst bed, and including the step of oxidatively or hydrogenatively regenerating said catalyst.

14. The process of claim 7 wherein said alkanol feedstock consists essentially of C₁–C₄ alkanol.

15. The process of claim 7 wherein step (a) conditions comprise a temperature of about 350° to 550° C., and a pressure of about 20 to 120 kPa.

16. The process of claim 7 wherein said feedstream comprises C₅ linear olefins.

17. A process for the production of methyl tertiary butyl ether from C₄ hydrocarbon stream rich in n-butene, comprising:

a) introducing a fresh liquid n-butene hydrocarbon feedstream into the top portion of a debutanizer fractionator above a solid acid catalyst bed first etherification zone contained therein under methanol and isobutene etherification reaction conditions while introducing step (c) reaction effluent into a bottom portion of said debutanizer, whereby a portion of said hydrocarbon feedstream is vaporized in contact with etherification reaction products to remove heat of etherification reaction and provide a debutanizer overhead vapor stream comprising n-butene plus a bottom liquid stream comprising methyl tertiary butyl ether;

b) contacting said overhead stream with acidic, ZSM-35 metallosilicate catalyst in an isomerization zone under n-butene isomerization conditions sufficient to convert said n-butene to isobutene, said conditions comprising a temperature of about 300° C. to 700° C., an olefin partial pressure between about 20 kPa and 500 kPa and between about 5 and 500 WHSV, whereby an effluent stream is produced rich in isobutene;

c) cooling and compressing step (b) reaction effluent and passing the cooled and compressed step (b) reaction effluent rich in isobutene and a methanol feedstream to a vapor phase iso-olefin second etherification zone in contact with acidic etherification catalyst under etherification conditions whereby a second etherification zone reaction effluent is produced comprising methyl tertiary butyl ether, unconverted methanol and isobutene;

d) introducing step (c) reaction effluent into step (a) debutanizer below said solid acid catalyst bed whereby step (c) unconverted methanol and isobutene are converted to methyl tertiary butyl ether.

18. The process of claim 17 including the further step of introducing fresh methanol in a bottom portion of said debutanizer.

19. The process of claim 1 wherein step (c) catalyst comprises synthetic ferrierite.

* * * * *